(12) United States Patent
Jiao et al.

(10) Patent No.: US 12,251,198 B2
(45) Date of Patent: Mar. 18, 2025

(54) VASOSPASM MONITORING DEVICE BASED ON TRIBOELECTRIFICATION TECHNOLOGY

(71) Applicant: ZHEJIANG UNIVERSITY, Zhejiang (CN)

(72) Inventors: Pengcheng Jiao, Zhejiang (CN); Yang Yang, Zhejiang (CN); Xiaoxiao Cui, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 763 days.

(21) Appl. No.: 17/611,181

(22) PCT Filed: Sep. 29, 2020

(86) PCT No.: PCT/CN2020/118681
§ 371 (c)(1),
(2) Date: Nov. 15, 2021

(87) PCT Pub. No.: WO2021/258574
PCT Pub. Date: Dec. 30, 2021

(65) Prior Publication Data
US 2022/0304581 A1    Sep. 29, 2022

(30) Foreign Application Priority Data
Jun. 24, 2020   (CN) .......................... 202010589335.7

(51) Int. Cl.
*A61B 5/02* (2006.01)
*A61B 5/00* (2006.01)
(Continued)

(52) U.S. Cl.
CPC ............ *A61B 5/02007* (2013.01); *A61B 5/05* (2013.01); *A61B 5/076* (2013.01); *A61B 5/6862* (2013.01); *H02N 1/04* (2013.01)

(58) Field of Classification Search
None
See application file for complete search history.

(56) References Cited

U.S. PATENT DOCUMENTS 10,307,065 B1    6/2019  Lovoi et al.
2011/0208067 A1*  8/2011  Edman ............... A61B 5/02007
                                          600/486
(Continued)

FOREIGN PATENT DOCUMENTS

CN    201361068    12/2009
CN    103389325    11/2013
(Continued)

OTHER PUBLICATIONS

English Translation KR-2020070030-Al, Song Dae-yoon, 4 pages, printed on Oct. 4, 2024, (Year: 2020).*

*Primary Examiner* — Devin B Henson
*Assistant Examiner* — Jennifer Grace Baires-Tweed
(74) *Attorney, Agent, or Firm* — JCIP GLOBAL INC.

(57) ABSTRACT

A vasospasm monitoring device based on a triboelectrification technology includes a vascular stent. A plurality of hole-shaped structures are distributed on the vascular stent. A triboelectric film sleeve is inserted into each hole-shaped structures in a matched mode, and the triboelectric film sleeve includes an inner electrode, an inner triboelectric material layer, an outer triboelectric material layer, and an outer electrode. The inner triboelectric material layer and the outer triboelectric material layer can generate electricity by friction, and the inner electrode and the outer electrode are electrically connected to a bioelectric signal processing patch.

7 Claims, 3 Drawing Sheets

(51) Int. Cl.
*A61B 5/05* (2021.01)
*A61B 5/07* (2006.01)
*H02N 1/04* (2006.01)

(56) References Cited

U.S. PATENT DOCUMENTS

2016/0344307 A1* 11/2016 Liu .......................... H02N 1/04
2017/0079814 A1* 3/2017 Kawashima ............ A61F 2/958

FOREIGN PATENT DOCUMENTS

| | | | |
|---|---|---|---|
| CN | 104811089 | 7/2015 | |
| CN | 105496388 | 4/2016 | |
| CN | 108513542 | 9/2018 | |
| CN | 109998474 | 7/2019 | |
| KR | 2020070030 A * | 6/2020 | ........... A61B 5/0215 |

* cited by examiner

VASOSPASM MONITORING DEVICE BASED ON TRIBOELECTRIFICATION TECHNOLOGY

CROSS-REFERENCE TO RELATED APPLICATION

This application is a 371 of international application of PCT application serial no. PCT/CN2020/118681, filed on Sep. 29, 2020 which claims the priority benefit of China application no. 202010589335.7, filed on Jun. 24, 2020. The entirety of each of the above mentioned patent applications is hereby incorporated by reference herein and made a part of this specification.

BACKGROUND

Technical Field

The present invention belongs to the technical field of triboelectrification, and in particular relates to a vasospasm monitoring device based on a triboelectrification technology.

Description of Related Art

Cardio-cerebrovascular diseases are the number one health killer, accounting for more than 30% of total worldwide deaths. In 2018, the number of patients suffering from cardio-cerebrovascular diseases in China was about 300 million, and deaths caused by cardio-cerebrovascular diseases account for more than 40% of disease death of residents, ranking first in all categories of diseases. The cardio-cerebrovascular diseases are usually associated with vascular stenosis or vascular occlusion. Current treatment means for cardiovascular diseases include drug therapy, surgical repair and autologous/allogeneic or artificial substitute transplantation, etc. With the progress of science and technology, more and more research on cardio-cerebrovascular diseases has been directed to the field of tissue engineering technology.

Tissue engineering is to apply principles and methods from engineering, material science, and life science to develop tissue substitutes with a certain biological activity by stimulating structures and functions of a target tissue, thus reconstructing, maintaining, and improving the physiological function of an affected tissue. Compared to the traditional treatment method, the tissue engineering technology has the advantages of being good in biocompatibility, capable of being produced in batches, high in size controllability, free of immune rejection and inflammatory response and the like. Vascular tissue engineering is intended to be able to prepare substitutions with similar properties to human tissue. An ideal tissue engineering vascular stent structure should have good biocompatibility and blood compatibility, and should also have certain mechanical properties and pore structures, thus meeting behaviors such as adhesion, proliferation, and migration of cells. Tissue vascular engineering stent materials are mainly divided into two major types of bio-based materials and non-bio-based materials, wherein the bio-based stent is formed by decellularization of natural tissues, and a large amount of collagen fibers and elastic fibers are reserved in the stent, thus the inflammation and immune response are not prone to being caused.

Triboelectric phenomenon and electrostatic phenomenon are particularly common phenomena in daily life, and due to the fact that the triboelectricity and static electricity are difficult to be collected and utilized, such energy form is often ignored by people. The existing triboelectricity is mainly applied to the fields of friction nano-generators, sensors, and the like. The present invention provides a vasospasm monitoring device based on a triboelectrification technology, when smooth muscle of a vascular wall contracts strongly, a lumen becomes narrow, the bio-based vascular stent structure contracts, and then a double-layer high-molecular polymer film generates a mechanical deformation to generate friction, thus achieving triboelectrification. An electric signal is transmitted to an external receiving device through a bioelectric signal processing patch, and the degree of vasospasm can be reflected, thus monitoring vasospasm and achieving timely warning.

SUMMARY

To overcome the defects of the prior art, the present invention provides a technical solution of a vasospasm monitoring device based on a triboelectrification technology.

The vasospasm monitoring device based on the triboelectrification technology comprises a vascular stent. A plurality of hole-shaped structures are distributed on the vascular stent. A triboelectric film sleeve is inserted into each hole-shaped structure in a matched mode, and the triboelectric film sleeve comprises an inner electrode, an inner triboelectric material layer, an outer triboelectric material layer and an outer electrode which are sequentially arranged from inside to outside in a sleeved mode. The inner triboelectric material layer and the outer triboelectric material layer can generate electricity by friction, and the inner electrode and the outer electrode are electrically connected to a bioelectric signal processing patch.

The vasospasm monitoring device based on the triboelectrification technology is provided, wherein the inner triboelectric material layer is a triboelectric cathode material layer, and the outer triboelectric material layer is a triboelectric anode material layer; or, the inner triboelectric material layer is a triboelectric anode material layer, and the outer triboelectric material layer is a triboelectric cathode material layer.

The vasospasm monitoring device based on the triboelectrification technology is provided, wherein the triboelectric film sleeve further comprises a protective film wrapping the inner electrode, the inner triboelectric material layer, the outer triboelectric material layer, and the outer electrode; and the protective film makes the triboelectric film sleeve be insulated from an external environment.

The vasospasm monitoring device based on the triboelectrification technology is provided, wherein the protective film comprises an inner protective film wrapping an inner side of the inner electrode and an outer protective film wrapping an outer side of the outer electrode, the inner protective film and the outer protective film are connected at both ends in an axial direction, such that the inner electrode, the inner triboelectric material layer, the outer triboelectric material layer and the outer electrode be completely wrapped therein.

The vasospasm monitoring device based on the triboelectrification technology is provided, wherein the inner electrode and the outer electrode are connected to the bioelectric signal processing patch through wires, and the wires are coated with insulating films.

The vasospasm monitoring device based on the triboelectrification technology is provided, wherein the bioelectric signal processing patch is wirelessly connected to an external signal acquisition terminal.

The vasospasm monitoring device based on the triboelectrification technology is provided, wherein a nanoscale wireless signal transmitting unit is arranged in the bioelectric signal processing patch, a wireless signal receiving unit is arranged in the external signal acquisition terminal, and the nanoscale wireless signal transmitting unit is wirelessly connected to the wireless signal receiving unit.

Compared with the prior art, the vasospasm monitoring device is suitable for monitoring blood vessels, and when smooth muscle of a vascular wall contracts strongly and a lumen becomes narrow, the vascular stent structure disclosed by the present invention contracts, then the triboelectric film sleeve generates a mechanical deformation to generate friction, thus achieving triboelectrification. An electric signal is transmitted to the external signal acquisition terminal through the bioelectric signal processing patch, and the electric signal is collected and analyzed by the external signal acquisition terminal, thus monitoring vasospasm and achieving timely warning, which is beneficial to human health.

DESCRIPTION OF THE EMBODIMENTS

Figure 1:
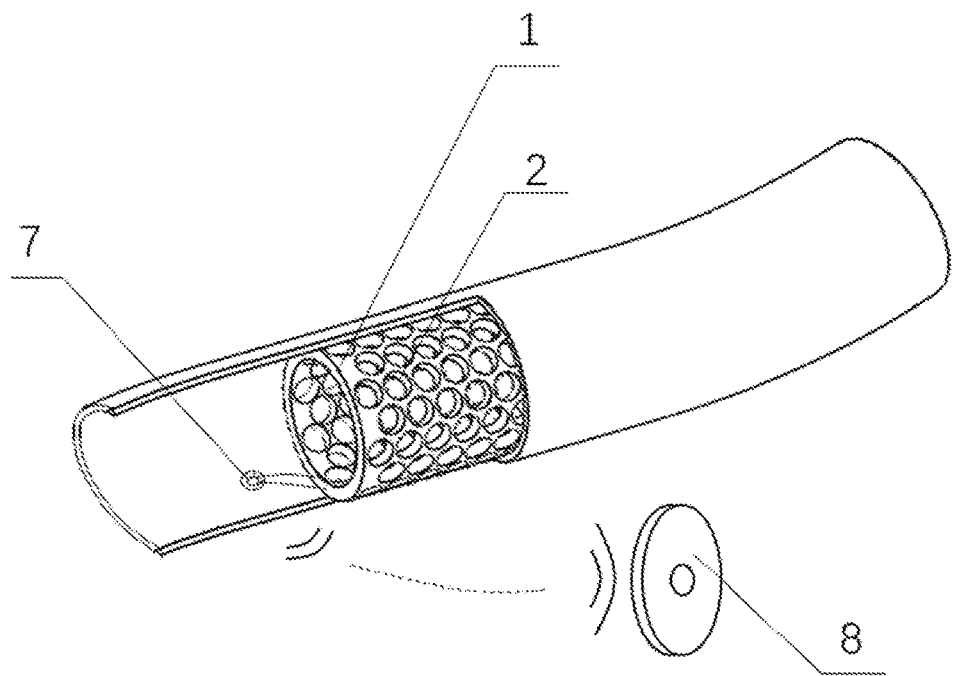
FIG. 1 is a structure diagram of a use state in accordance with the present invention when used in blood vessels.

The present invention is further described below in conjunction with the accompanying drawings.

As shown in the figures, a vasospasm monitoring device based on a triboelectrification technology is provided. The vasospasm monitoring device comprises a vascular stent 1. A plurality of hole-shaped structures 2 are distributed on the vascular stent 1. A triboelectric film sleeve 4 is inserted into each hole-shaped structure 2 in a matched mode, and is an annular layered structure matched with the shape of the hole-shaped structure. The triboelectric film sleeve 4 comprises an inner electrode 41, an inner triboelectric material layer, an outer triboelectric material layer and an outer electrode 44 which are sequentially arranged from inside to outside in a sleeved mode. The inner triboelectric material layer and the outer triboelectric material layer can generate electricity by friction, and the inner electrode 41 and the outer electrode 44 are electrically connected to a bioelectric signal processing patch 7. The inner triboelectric material layer is a triboelectric cathode material layer 42, and the outer triboelectric material layer is a triboelectric anode material layer 43.

The following changes can be made in the present invention, the inner triboelectric material layer is a triboelectric anode material layer 43, and the outer triboelectric material layer is a triboelectric cathode material layer 42.

Preferably, the triboelectric film sleeve 4 further comprises a protective film wrapping the inner electrode 41, the inner triboelectric material layer, the outer triboelectric material layer, and the outer electrode 44, and the protective film makes the triboelectric film sleeve 4 be insulated from an external environment.

In above structure, the protective film comprises an inner protective film 40 wrapping an inner side of the inner electrode 41, and an outer protective film 45 wrapping an outer side of the outer electrode 44, the inner protective film 40 and the outer protective film 45 are connected by pressure welding or adhesion at both ends of an axial direction, thus making the inner electrode 40, the inner triboelectric material layer, the outer triboelectric material layer and the outer electrode 44 be completely wrapped therein.

Preferably, the inner electrode 41 and the outer electrode 44 are connected to the bioelectric signal processing patch 7 through wires, and the wires are coated with insulating films.

Preferably, the bioelectric signal processing patch 7 is wirelessly connected to an external signal acquisition terminal 8.

In above structure, a nanoscale wireless signal transmitting unit is arranged in the bioelectric signal processing patch 7, a wireless signal receiving unit is arranged in the external signal acquisition terminal, and the nanoscale wireless signal transmitting unit is wirelessly connected to the wireless signal receiving unit.

In the present invention, the external signal acquisition terminal 8 may be electronic terminals such as mobile phones, bracelets, watches, and the like, which can acquire, process, and analyze electric signals acquired by the bioelectric signal processing patch 7.

In the present invention, the vascular stent 1 may be a bio-based vascular stent formed by decellularization of natural tissues, and a large amount of collagen fibers and elastic fibers are reserved in the stent, thus the inflammation and immune response are not prone to being caused. When smooth muscle of a vascular wall contracts strongly, a lumen becomes narrow, the vascular stent 1 contracts, then the hole-shaped structures 2 on the structure generate deformations, the triboelectric film sleeve 4 in each hole-shaped structure 2 may generate a mechanical deformation, and the triboelectric cathode material layer 42 and the triboelectric anode material layer 43 may be in friction with each other to generate a positive current under the action of an external circuit. A negative current is generated by the inner electrode 41 and the outer electrode 44 under the action of electrostatic induction.

The triboelectric anode material 43 in the present invention is specifically made of polyethylene terephthalate (PET), and the triboelectric cathode material 42 is specifically made of Polyimide (Kapton). The triboelectric anode material 43 may also be made of nylon, and correspondingly, the triboelectric cathode material 42 may be made of polytetrafluoroethylene. In addition, a triboelectric anode material film 5 and a triboelectric cathode material film 6 may also be other material combinations with triboelectric functions.

The present invention is explained by taking FIG. 1 as an example. An ideal bio-based tissue engineering vascular stent structure should have good biocompatibility and blood compatibility, and should also have certain mechanical properties and pore structures, thus meeting behaviors such as adhesion, proliferation, and migration of cells. Therefore, by utilizing the vascular stent with the hole-shaped structures, the present invention proposes to arrange triboelectric materials in the hole-shaped structures, when the triboelectric materials generate mechanical deformations, friction is generated between the materials, and charge separation is generated to form potential differences. Metal electrodes are arranged at two sides of the triboelectric material, and a current is generated under the driving of an external circuit, thus achieving triboelectrification.

Figure 2:
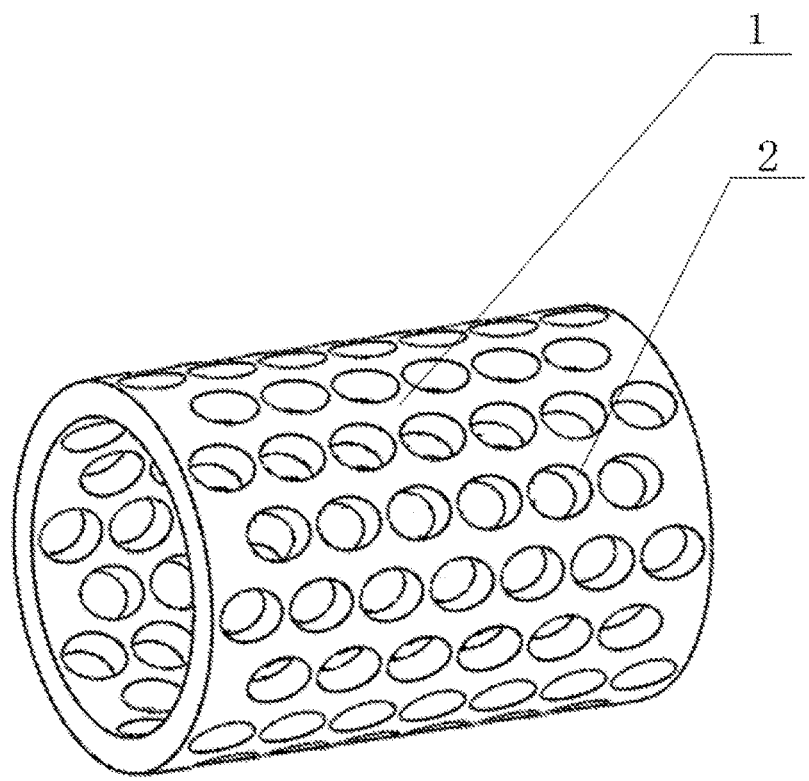
FIG. 2 is a structure diagram of a vascular stent in accordance with the present disclosure.
Figure 3:
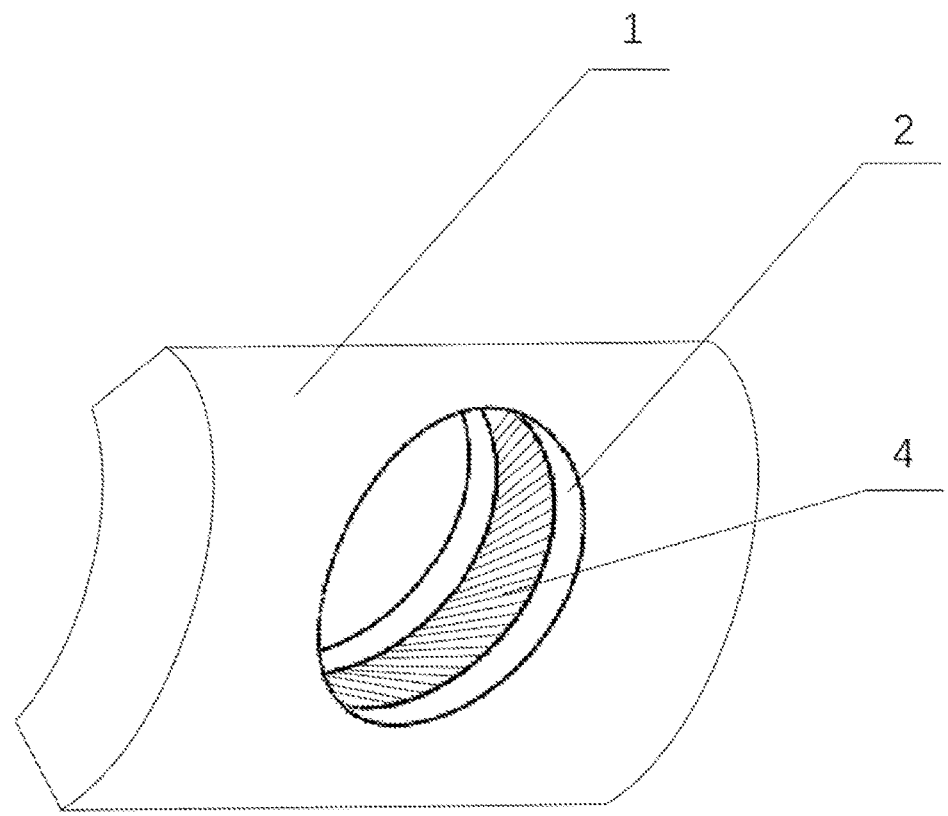
FIG. 3 is a first diagram of a hole-shaped structure in accordance with the present invention, where the porous structure is circular.
Figure 4:
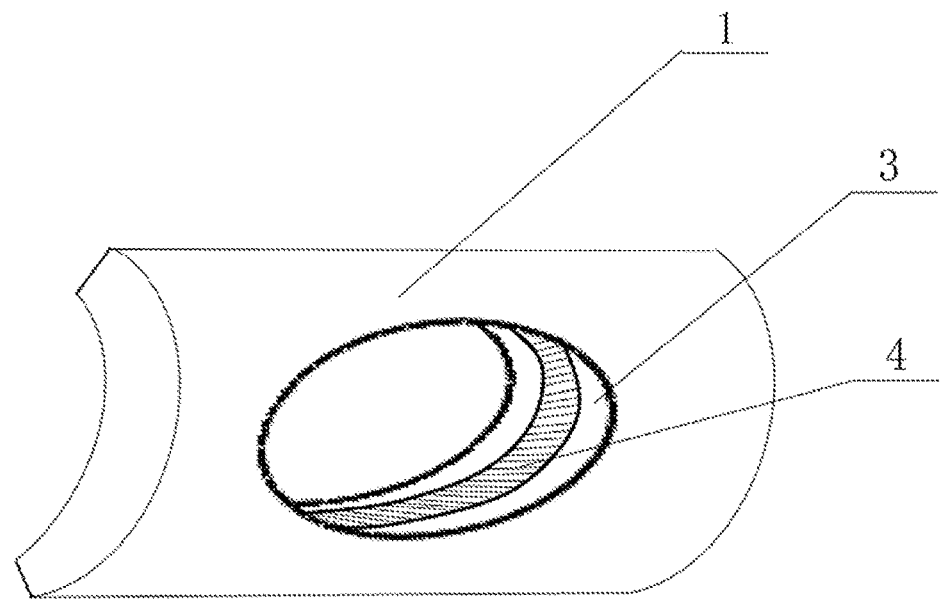
FIG. 4 is a second diagram of a hole-shaped structure in the present invention, where the porous structure is oval.

FIG. 2 shows the change of a vascular stent structure when the bio-based vascular stent structure contracts. When the smooth muscle of the vascular wall contracts strongly, the lumen becomes narrow, and the bio-based vascular stent structure contracts. FIG. 3 and FIG. 4 show that the vascular stent is deformed, if the hole-shaped structure is changed from a circular hole-shaped structure to an oval hole-shaped structure, the triboelectric film sleeve 4 arranged in the hole-shaped structure generates mechanical deformation to generate triboelectric current.

Figure 5:
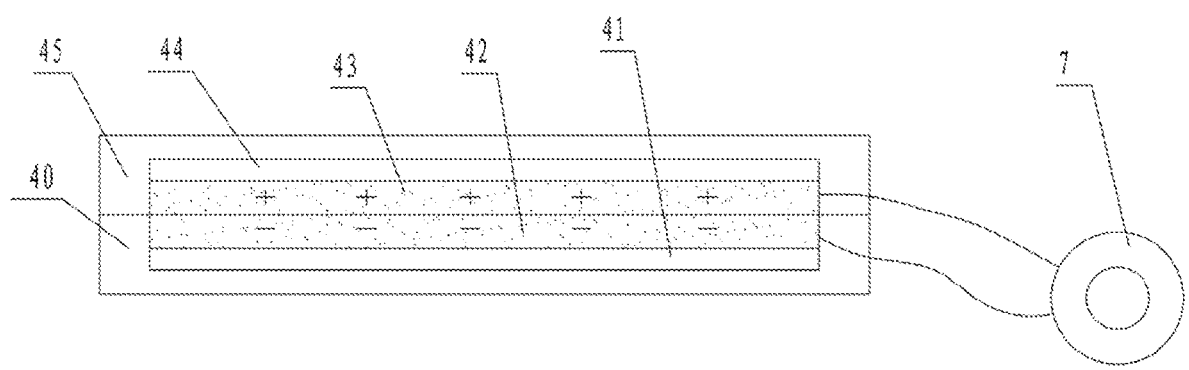
FIG. 5 is a diagram of a layered structure of a triboelectric film sleeve in accordance with the present invention.

FIG. 5 specifically explains a triboelectric film sleeve 4 and a working principle of an external circuit thereof. When the double-layer high-molecular polymer film generates mechanical deformation, the triboelectric cathode material layer 42 is in friction with the triboelectric anode material layer 43, and the friction makes the generation of charge separation between the materials to produce the positive current. The metal electrodes are electrified due to charging by induction, a negative current is generated under the action of the external circuit, and the charge is finally neutralized, thus completing once triboelectrification process.

Finally, it should be noted that the above embodiments are merely illustrative of the technical solutions of the present invention, and are not intended to limit the same. Although the present invention has been described in detail with reference to the foregoing embodiments, it should be understood by those of ordinary skill in the art that modification may be made to the technical solutions described in the foregoing embodiments, or equivalent replacement may be made to some or all of the technical features; and the modifications or replacements do not make the essence of the corresponding technical solutions deviate from the scope of the technical solutions of various embodiments of the present invention.

What is claimed is:

1. A vasospasm monitoring device based on a triboelectrification technology, the vasospasm monitoring device comprising a vascular stent, wherein a plurality of hole-shaped structures are distributed on the vascular stent, a triboelectric film sleeve is configured to be inserted into each hole-shaped structure in a matched mode, and the triboelectric film sleeve comprises an inner electrode, an inner triboelectric material layer, an outer triboelectric material layer and an outer electrode which are sequentially arranged from inside to outside in a sleeved mode; the inner triboelectric material layer and the outer triboelectric material layer are able to generate electricity by friction, and the inner electrode and the outer electrode are electrically connected to a bioelectric signal processing patch.

2. The vasospasm monitoring device based on the triboelectrification technology according to claim 1, wherein the inner triboelectric material layer is a triboelectric cathode material layer, and the outer triboelectric material layer is a triboelectric anode material layer; or, the inner triboelectric material layer is a triboelectric anode material layer, and the outer triboelectric material layer is a triboelectric cathode material layer.

3. The vasospasm monitoring device based on the triboelectrification technology according to claim 1, wherein the triboelectric film sleeve further comprises a protective film wrapping the inner electrode, the inner triboelectric material layer, the outer triboelectric material layer, and the outer electrode; and the protective film makes the triboelectric film sleeve be insulated from an external environment.

4. The vasospasm monitoring device based on the triboelectrification technology according to claim 3, wherein the protective film comprises an inner protective film wrapping an inner side of the inner electrode and an outer protective film wrapping an outer side of the outer electrode, the inner protective film and the outer protective film are connected at both ends in an axial direction, such that the inner electrode, the inner triboelectric material layer, the outer triboelectric material layer and the outer electrode are completely wrapped in the protective film.

5. The vasospasm monitoring device based on the triboelectrification technology according to claim 1, wherein the inner electrode and the outer electrode are connected to the bioelectric signal processing patch through wires, and the wires are coated with insulating films.

6. The vasospasm monitoring device based on the triboelectrification technology according to claim 1, wherein the bioelectric signal processing patch is wirelessly connected to an external signal acquisition terminal.

7. The vasospasm monitoring device based on the triboelectrification technology according to claim 6, wherein a nanoscale wireless signal transmitting unit is arranged in the bioelectric signal processing patch, a wireless signal receiving unit is arranged in the external signal acquisition terminal, and the nanoscale wireless signal transmitting unit is wirelessly connected to the wireless signal receiving unit.

* * * * *